United States Patent [19]

Dahlgren

[11] Patent Number: 4,901,375
[45] Date of Patent: Feb. 20, 1990

[54] MALE URINAL APPLIANCE

[76] Inventor: Marcella Dahlgren, 1811 Lakehurst Dr., Nashville, Tenn. 37206

[21] Appl. No.: 163,304
[22] Filed: Mar. 2, 1988
[51] Int. Cl.⁴ ............................................. A47K 11/00
[52] U.S. Cl. ..................................... 4/144.3; 224/222; 224/229; 604/353
[58] Field of Search .................. 4/144.1, 144.2, 144.3, 4/144.4, 114.1; 224/222, 226, 229, 250, 253, 148; 604/353, 345, 351, 349; 220/94 A, DIG. 13; 215/100 A

[56] References Cited

U.S. PATENT DOCUMENTS

| D. 217,439 | 5/1970 | Platte | 220/94 A |
|---|---|---|---|
| 1,801,030 | 4/1931 | Vasse | 4/144.1 |
| 2,524,639 | 10/1950 | Saunders | 224/250 |
| 2,542,276 | 2/1951 | Felts | 4/144.3 |
| 2,594,339 | 4/1952 | Nugent | 4/144.1 |
| 2,756,751 | 7/1956 | Smith | 604/353 |
| 2,840,079 | 6/1958 | Conway et al. | 604/353 |
| 3,030,636 | 4/1962 | Evans | 4/144.3 |
| 3,035,579 | 5/1962 | Benovic | 604/353 |
| 3,604,424 | 9/1971 | Windom | 604/353 |
| 3,716,871 | 2/1973 | Borse | 4/144.2 |
| 3,727,244 | 4/1973 | Collins | 4/144.3 |
| 4,050,103 | 9/1977 | Nakao et al. | 4/144.3 |
| 4,073,295 | 2/1978 | Laufbahn | 604/353 |
| 4,117,845 | 10/1978 | Brown | 604/353 |
| 4,270,231 | 6/1981 | Zint | 4/144.1 |
| 4,420,104 | 12/1983 | DiIenno | 224/250 |
| 4,511,358 | 4/1985 | Johnson, Jr. et al. | 604/353 |
| 4,665,571 | 5/1987 | Muccione | 4/144.1 |

FOREIGN PATENT DOCUMENTS

| 21755 | 9/1910 | United Kingdom | 4/144.4 |
|---|---|---|---|
| 357455 | 9/1931 | United Kingdom | 4/144.4 |

Primary Examiner—Linda J. Sholl
Attorney, Agent, or Firm—Mark J. Patterson

[57] ABSTRACT

An improved male urinal appliance worn by incontinent male patients has a plastic urinal bottle with specially contoured neck and reservoir portions and an adjustable support belt for comfortably securing the bottle to an ambulatory or bedridden patient.

2 Claims, 2 Drawing Sheets

MALE URINAL APPLIANCE

BACKGROUND OF THE INVENTION

The present invention relates to a re-usable urinal appliance to be worn by male patients who are incontinent or otherwise bedridden. More specifically, the present invention includes a specially contoured bottle and support belt adapted to provide a comfortable, secure, hygienic and leak resistant means for collecting urine from bedridden or ambulatory patients who are incontinent.

A common, persistent, and difficult problem found in the elderly, in stroke victims, and in others, is dealing with long term urinary incontinence. The use of internal catheters in male patients is an excellent response to this problem, except that they are prone to cause infections if used for extended periods. External catheters are also used with some success, but they do not stay in place unless awkwardly secured. They are either irritable to the patient's skin, leak, have insufficient holding capacity, or are uncomfortable to wear, particularly for ambulatory patients.

What is needed, then, is a re-usable male urinal appliance that can be securely and comfortably worn by patients who must change position and than can hold adequate volume of urine without leaking.

SUMMARY OF THE INVENTION

The present invention comprises a specially contoured, light-weight plastic urinal reservoir bottle and a separate adjustable support belt. The neck of the bottle is angled, shaped, and beveled to minimize direct or reflux leakage, patient discomfort, and irritation. The upper portion of the bottle is shaped to provide a hand grip for ease in removal. The lower portion of the bottle is contoured to allow for wearing it comfortably between or next to the patient's leg or body, depending upon the needs of the patient. The bottle has two flat surfaces so that it can rest on a bed when the patient is not ambulatory. It is also adaptable for use with weights to assist in holding it in position with the bedridden patient.

The support belt has adjustable straps so that the appliance can be moved to a variety of positions and a pouch which conforms to and carries the bottle. The pouch opens at both the top and the bottom to facilitate changing the bottle while the appliance is in use.

DESCRIPTION OF THE PREFERRED EMBODIMENT

Figure 1:
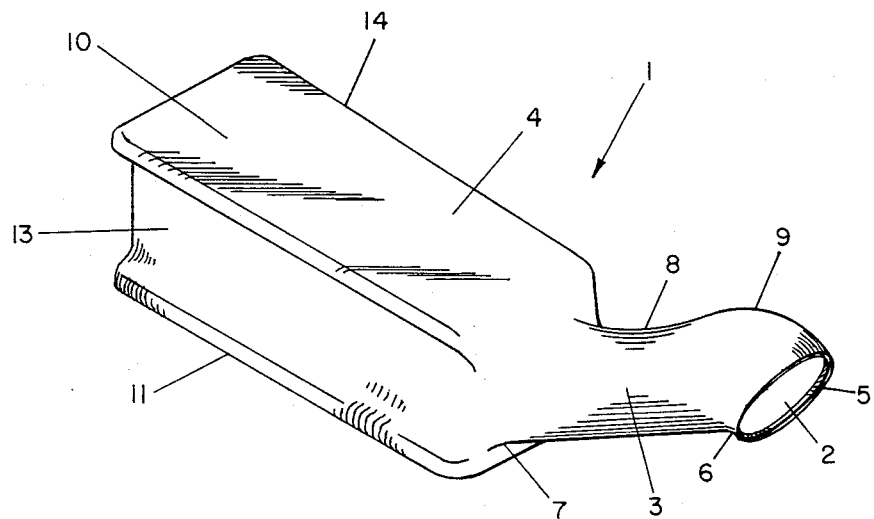
FIG. 1 is a perspective view of the urinal appliance bottle detached from its support belt.
Figure 2:
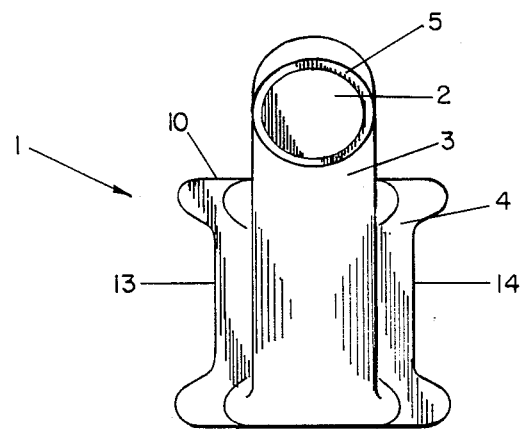
FIG. 2 is a front view of the urinal appliance bottle showing the special contours of the reservoir and neck areas.
Figure 3:
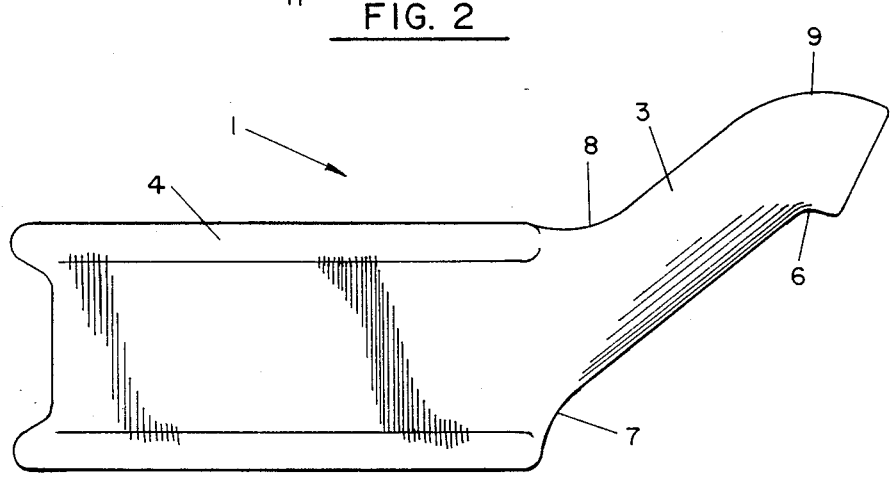
FIG. 3 is a side view of the urinal appliance bottle, again showing the special contours of the neck and reservoir areas.

As best seen on FIGS. 1, 2 and 3, a urinal bottle 1 molded of a clear, lightweight plastic comprises circular orifice 2, neck 3, and reservoir 4. Orifice 2, which is generally 2 smaller (approximately 1⅜ inches in diameter) than the openings in urinal bottles found in the prior art, helps provide a relatively leak-proof seal between the bottle and wearer. Beveled edge 5 minimizes irritation. In addition to the size of orifice 2, the unique contours and angles of neck 3 contribute significantly to the ability of bottle 1 to remain comfortably in place regardless of the position of the patient and to minimize urinary reflux out of the bottle, even without the use of an anti-reflux valve. Specifically, neck 3 is provided in the general case with contours in areas 6, 7, 8, and 9, with radii of curvature substantially and approximately as shown on FIGS. 2 and 3. Of course, these contours can vary somewhat, without departing from the spirit of the invention, depending upon the anatomical characteristics of the more unusual patient.

Figure 5:
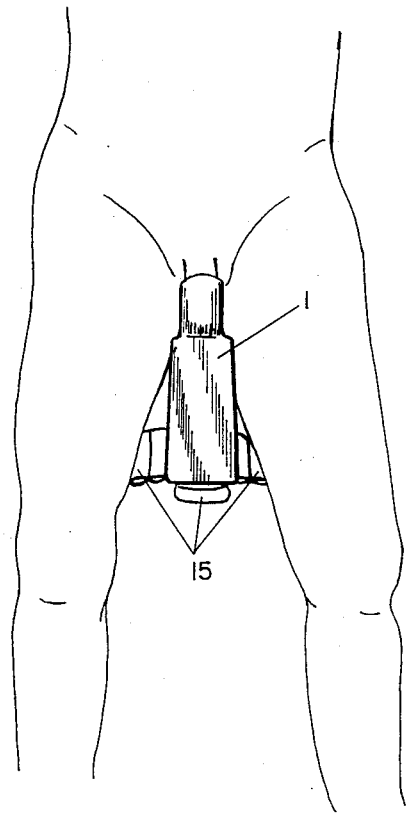
FIG. 5 shows the urinal bottle positioned on the bedridden patient secured with weights.

As best seen in FIG. 1, the uppermost portion of reservoir 4 is contoured to provide a grip-like shape to facilitate manual handling of bottle 1. Upper surface 10 and lower surface 11 of reservoir area 4 are flat so that the bottle can lay flat against the bed when the patient is supine, as seen in FIG. 5. Side surfaces 13 and 14 are contoured so that the bottle can be comfortably secured against or between the wearer's legs as in FIGS. 6 and 7. Again, recognizing that some variation may be necessary in unusual anatomical cases, the contours of the side surfaces 13 and 14 are substantially and approximately defined by the dimensions and curvatures shown on FIGS. 1, 2, and 3 and have been found to significantly improve the comfort and security of the present invention over the prior art.

Bottle 1 is made of a relatively clear material so that nursing personnel can quickly determine if it is full or if unusual color or sediment is present. Also, a scale, as seen on FIG. 3, is provided on the surface of the bottle 1, so that the volume of urine in the reservoir 4 can be accurately visualized.

When the bedridden patient is relatively immobile, the bottle 1 can be secured in place by use of weights 15, which are similar to small sandbags, as shown in FIG. 5.

Figure 4:
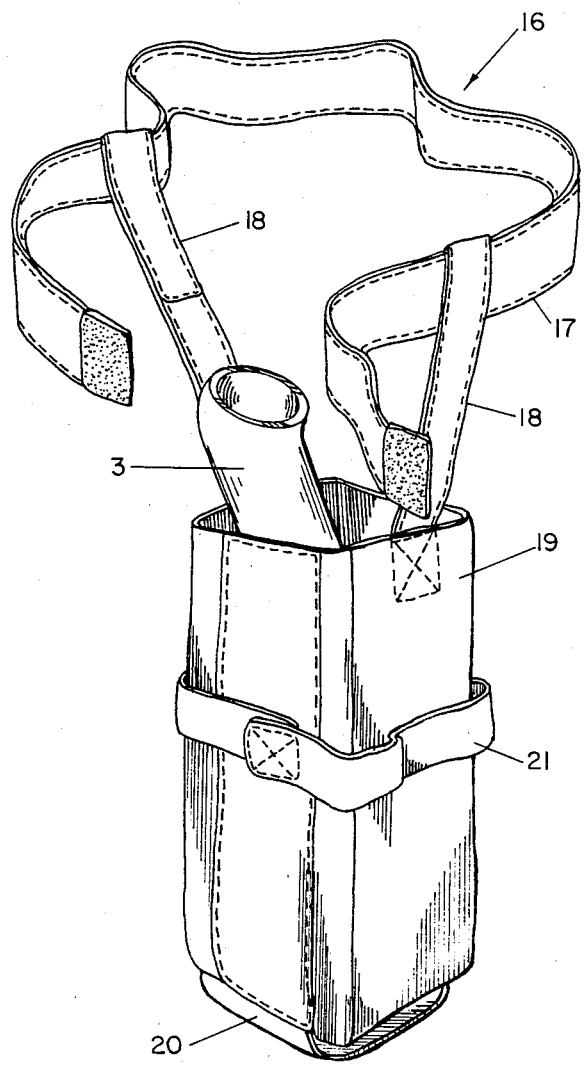
FIG. 4 is a perspective view of the bottle installed in its support belt.
Figure 6:
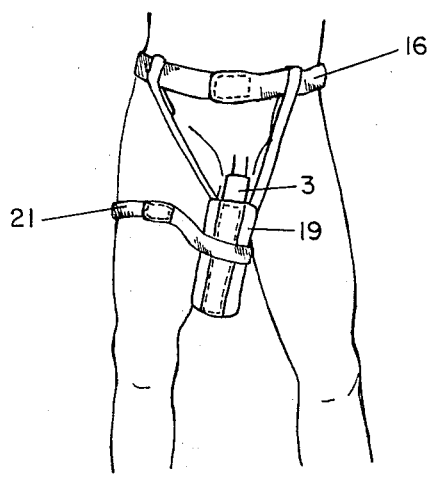
FIG. 6 shows the urinal appliance secured between an ambulatory patient's legs with the support belt.
Figure 7:
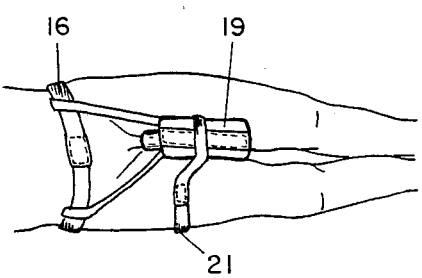
FIG. 7 shows the urinal appliance secured to a patient's leg who is on his side in bed.

For the patient who is ambulatory or who is repositioned while in the bed, as shown in FIGS. 6 and 7, respectively, support belt 16 is used, best seen on FIG. 4, comprising generally adjustable waist strap 17, adjustable vertical straps 18, and bottle pouch 19, all made of a washable, relatively smooth textured and flexible fabric material. Also, it has been found that the width of strap 17 should be at least approximately 2 inches to minimize belt rolling problems found in the prior art.

Bottle pouch 19, which supports bottle 1 in use, is open at the top and, by moving flap 20, can be opened at the bottom so that bottle 1 can be easily changed without removing support belt 16. Pouch 19 is generally rectangular in shape to conform to the shape of bottle 1, while strap 21 firmly secures bottle 1 within pouch 19 and to the patient's leg.

Adjustable waist strap 17 secures the appliance to the patient's waist, with adjustable straps 18 used to properly position bottle 1 vertically. The respective end portions of straps 17, 18, and 21 and flap 20 are fitted with VELCRO-type or hook and loop fabric patches to facilitate attachment, adjustment, and removal of belt 16. When properly adjusted, belt 16 and the previously described contours of bottle 1 combine to provide a significant improvement over the prior art in comfort and security for the incontinent patient, while minimizing expense and risk of infection. The inventor has found that the present invention will keep an incontinent stroke victim dry 95% of the time, which is a significant improvement over other appliances which she has tried.

What I claim is:

1. An improved male urinal appliance comprising in combination:
   (a) a circular orifice for receptively engaging the wearer and receiving the urine to be collected, said orifice having a beveled edge for reducing irritation;
   (b) a neck joining said orifice with a reservoir and substantially radially contoured such that such said orifice is higher than said reservoir so as to minimize direct or reflux leakage, maximize comfort and to allow said bottle to rest on a flat surface while still effectively engaging the wearer;
   (c) said reservoir having flat upper and lower surfaces and contoured side surfaces to comfortably engage the wearers body to fit in between wearers legs;
   (d) a support belt adapted for carrying and securing said bottle to the wearer comprising an adjustable leg strap, adjustable vertical straps, and bottle retaining pouch; and
   (e) where said bottle retaining pouch comprises a flap means for removing said bottle from the bottom of said pouch.

2. The appliance of claim 1 where the upper portion of said reservoir of said bottle, where it joins said neck, defines an integrally molded handle grip to facilitate handling of said bottle.

* * * * *